United States Patent [19]

Smith

[11] Patent Number: 5,540,650
[45] Date of Patent: Jul. 30, 1996

[54] BORESCOPE

[75] Inventor: Nigel C. Smith, Essex, United Kingdom

[73] Assignee: Keymed (Medical & Industrial Equipment) Limited, Essex, United Kingdom

[21] Appl. No.: 271,463

[22] Filed: Jul. 7, 1994

[30]    Foreign Application Priority Data

Jul. 26, 1993 [GB] United Kingdom ............... 9315445

[51] Int. Cl.$^6$ ................. A61B 1/002; G01N 21/00
[52] U.S. Cl. ................. 600/163; 600/137; 600/173; 356/241
[58] Field of Search ............... 128/4–6; 356/241; 385/902, 117, 119; 359/367; 600/130, 137, 163, 167, 170, 173

[56]    References Cited

U.S. PATENT DOCUMENTS

| | | | |
|---|---|---|---|
| 2,779,327 | 1/1957 | Baker | 128/6 |
| 2,990,830 | 7/1961 | Hett | 128/4 |
| 3,005,452 | 10/1961 | Pitman | 359/367 |
| 3,096,756 | 7/1963 | Rosenfeld et al. | 359/367 |
| 3,257,902 | 6/1966 | Hopkins | 359/367 |
| 4,061,135 | 12/1977 | Widran et al. | 128/6 |
| 4,685,450 | 8/1987 | Collins et al. | 128/4 |
| 4,798,451 | 1/1989 | Fujiwara | |
| 4,924,853 | 5/1990 | Jones et al. | |
| 5,005,943 | 4/1991 | Fort | |

FOREIGN PATENT DOCUMENTS

| | | |
|---|---|---|
| 355308 | 8/1961 | Switzerland . |
| 502561 | 3/1939 | United Kingdom . |
| 672579 | 5/1952 | United Kingdom . |
| 1155390 | 6/1969 | United Kingdom . |
| 1272742 | 5/1972 | United Kingdom . |
| 1568161 | 5/1980 | United Kingdom . |
| 2037002 | 7/1980 | United Kingdom . |
| 2068583 | 8/1981 | United Kingdom . |
| 2187303 | 9/1987 | United Kingdom . |

*Primary Examiner*—Richard J. Apley
*Assistant Examiner*—John P. Leubecker
*Attorney, Agent, or Firm*—Beveridge, Degrandi, Weilacher & Young, LLP

[57]    ABSTRACT

A borescope has an inverting dove prism (24) mounted on an ocular mount (12) proximally of an ocular lens (11). The ocular mount is axially adjustable by rotation of a collar (26) to achieve focusing and is rotatable about the axis independently of the focus position in unison with orbital scanning of a reflector (7) at the distal end of the borescope. Location of the dove prism proximally of the ocular lens avoids the need to include an invertor within the optical relay of insertion tube (2) thereby avoiding aperture reduction and simplifying assembly.

15 Claims, 1 Drawing Sheet

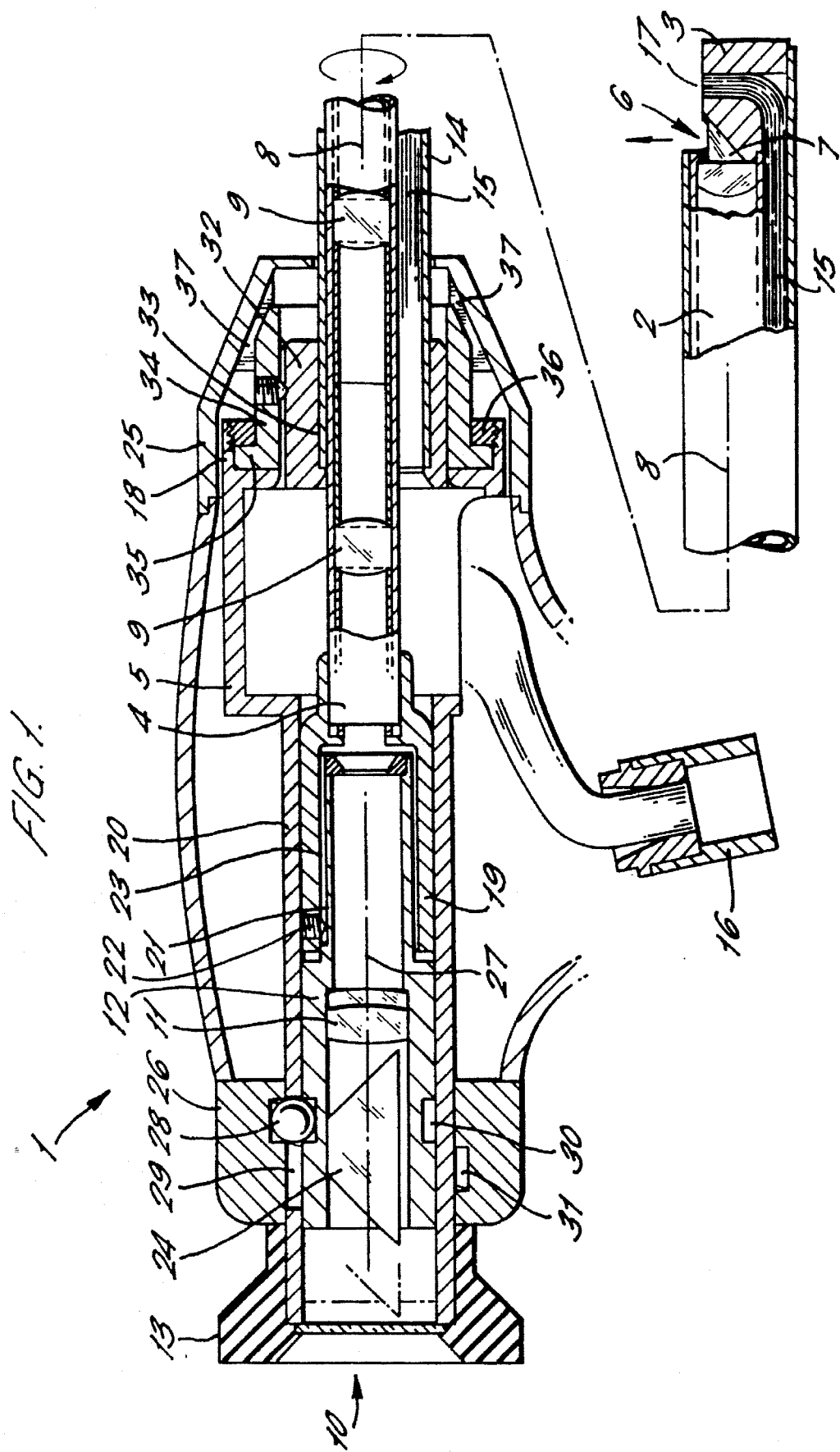

BORESCOPE

BACKGROUND OF THE INVENTION

This invention relates to apparatus for use as a borescope of the orbital scanning type.

It is known to provide such borescopes in which a reflector is rotatably mounted to achieve lateral viewing in a direction which can be orbitally scanned. Typically the reflector is associated with a window at a distal end of a tube of the borescope suitable for insertion into inaccessible areas, the tube typically containing an optical relay which transfers an image reflected by the reflector to a viewing means within a housing to which the tube is connected.

Since the reflector provides a mirror image of the object being viewed it is customary to include an image inverter such as a dove prism to correct the image and typically such an inverter is included within the tube as part of the optical relay. A disadvantage of such an arrangement is that when positioning the inverter between the lenses of the optical relay the size of the inverter is limited to that of the diameter of the relay lenses. Its shape then restricts the amount of light that can be transmitted through the optical relay or in other words the effective aperture of the inverter is less than that of the optical relay. The brightness of the viewed image is thereby reduced.

A further problem is that the performance of the borescope is sensitive to any slight misalignment of the inverter thereby creating difficulties in achieving correct assembly during manufacture since readjustment may require disassembly of the optical relay.

It is an object of the present invention to provide such apparatus with improved image brightness and to simplify its assembly.

SUMMARY OF THE INVENTION

According to the present invention there is disclosed apparatus for use as a borescope comprising a tube having a distal end which is insertable in use into an inaccessible location and a proximal end connected to a housing, a viewing port adjacent the distal end and an associated reflector through which an object at the inaccessible location may be laterally viewed in use, an image relaying means operable to relay an image of the object to a viewing means provided in the housing, a scanning means operable to rotate the reflector relative to the housing about a rotation axis extending longitudinally of the tube, focusing means operable to adjust the position of the viewing means relative to the housing in the direction along an optical axis defined by the viewing means and an image inverter operable to correct image inversion created by the reflector, wherein the inverter is rotatably mounted in the housing for rotation about the optical axis, the scanning means is further operable to provide the rotation of the inverter synchronously with the rotation of the reflector, and wherein the viewing means comprises an ocular lens received in an ocular mount with respect to which the inverter is fixedly connected at a location proximal to the ocular lens.

An advantage of such apparatus is that since the inverter is located within the housing its size is not limited by the space available within the tube and it can therefore be arranged to have an effective aperture which is sufficiently large so as to have no limiting effect on the overall performance of the borescope.

A further advantage is that the tube can be assembled with the image relaying means in the absence of an inverter thereby simplifying assembly. The adjustment of the inverter can be separately effected without needing to address the difficulties of assembly within the tube.

Conveniently the scanning means is operable to rotate the ocular mount about the optical axis to provide rotation of the inverter.

Preferably the focusing means comprises a focus actuator operable to provide adjustment along the optical axis of the position of the ocular mount relative to the housing.

By this arrangement the relative position of the inverter and ocular lens remains unchanged.

Preferably the ocular mount is slidably received in a tubular portion of the housing and the focus actuator comprises a collar rotatably mounted on the tubular portion, the apparatus further comprising a coupling mechanism operable to axially displace the ocular mount in response to rotation of the collar and allowing the ocular mount to rotate freely relative to the collar in response to rotation of the ocular mount by the scanning means.

Conveniently the coupling mechanism comprises a ball bearing located in an axially extending slot defined by the tubular portion of the housing, the ball bearing projecting radially inwardly and outwardly of the tubular portion into respective engagement with an annular groove formed in a cylindrical surface of the ocular mount and a helical groove formed in the collar.

In a preferred embodiment the scanning means is operable to rotate the tube relative to the housing such that the rotation axis of the tube is colinear with the optical axis of the viewing means, the tube being provided with a connecting member operable to impart rotational movement of the tube to synchronous rotational movement of the ocular mount, one of the connecting member and the ocular mount being provided with an axially extending slot cooperable with a radially projecting pin mounted on the other.

Conveniently the image relaying means comprises an optical relay having a plurality of lenses spaced axially within the tube.

In a preferred embodiment the inverter comprises a dove prism.

The effective aperture of the dove prism is preferably at least as large as the effective aperture of the ocular lens.

BRIEF DESCRIPTION OF THE DRAWING

A preferred embodiment of the present invention will now be described by way of example only with reference to the accompanying drawing of which FIG. 1 is a longitudinal section of a borescope in accordance with the present invention.

DETAILED DESCRIPTION OF THE PREFERRED EMBODIMENTS OF THE INVENTION

In FIG. 1 a borescope 1 comprises a tube 2 having a distal end 3 and a proximal end 4 received within a housing 5.

A side viewing port 6 is provided at the distal end 3 of the tube 2 and a prismatic reflector 7 is located adjacent the viewing port 6 so as to reflect light from a laterally located object in the general direction of a longitudinal axis 8 defined by the tube. The tube 2 contains axially spaced relay lenses 9 which together comprise an optical relay operable to relay an image of an object being viewed through the tube to a viewing means 10 within the housing 5.

The viewing means 10 includes an ocular lens 11 mounted in a cylindrical ocular mount 12 and further includes an eye piece assembly 13.

The tube 2 is contained within a tubular shaft 14 within which it is eccentrically located to accomodate a fibre optic bundle 15 of crescent shaped cross section which conducts light from a light guide connector 16 to an illumination port 17 adjacent the distal end 3. Light emerging from the illumination port 17 is thereby available to illuminate an object to be viewed. The shaft 14 has a relatively narrow external diameter thereby making it suitable for insertion into inaccessible areas.

The tube 2 extends coaxially through a bearing 18 of the housing 5 and is connected to a tubular connecting member 19 of enlarged diameter which forms a proximally projecting extension to the tube.

The connecting member 19 is slidably received within a tubular portion 20 of the housing 5. The ocular mount 12 is similarly received as a sliding fit within the tubular portion 20 such that the ocular lens 11 is spaced proximally from the connecting member 19. The ocular mount 12 includes a distally projecting tubular projection 21 which extends within the connecting member 19. A cone point screw 22 threaded in connecting member 19 engages in axially extending slot 23 formed in tubular projection 21. Thus, the ocular mount 12 and connecting member 19 are rotatably fixed such that they rotate at a common rate upon rotation of scanning actuator 25. The depth of the cone point screw is such that relative rotational movement between the tubular projection 21 and the connecting member 19 is prevented while allowing axial movement accomodated by displacement of the screw along the slot.

A dove prism 24 is mounted within the ocular mount 12 so as to be proximally adjacent to the ocular lens 11. The dove prism is oriented to correct image inversion resulting from reflection by the reflector 7.

The tube 2 is mounted in the bearing 18 by means of a bush 32 defining an eccentric bore 33 into which the shaft 14 is located, the eccentricity of the bore 33 being such that the outer cylindrical surface of the bush 32 defines a cylindrical axis coincident with the longitudinal axis 8 of the tube 2.

The bush 32 is in turn secured within an annular fitting 34 which is journalled in the bearing 18, the bush having a flange 35 which is captively retained within the bearing 18 by a locking ring 36. A scanning actuator 25 is manually rotatable relative to the housing 5 and is connected by webs 37 to the fitting 34.

The tube 2 is thereby received in the bearing 18 in a manner which prevents axial movement of the tube relative to the housing 5 but which allows rotational movement of the tube about the longitudinal axis 8 in response to actuation by a user turning the scanning actuator 25.

Because of the above described connection between the connecting member 19 and the ocular mount 12, rotation of the scanning actuator 25 results not only in rotation of the tube and with it the reflector 7 but also synchronous rotation of the ocular mount and with it the dove prism 24. In this way any rotational movement of the reflector 7 to a new scanning position is accompanied synchronously by appropriate movement of the dove prism 24 thereby ensuring continued correction of the inverted image.

The focusing of the borescope 1 is accomodated by means of turning an annular collar 26 which is rotatably mounted on the tubular portion 20 of the housing 5. The collar 26 is coupled to the ocular mount 12 in a manner which converts rotational movement of the collar into axial movement of the ocular mount 12 along a direction coincident with an optical axis 27 defined by the ocular lens 12.

This coupling is achieved by means of a ball bearing 28 received within an axially extending slot 29 formed in the tubular portion 20. The ball bearing 28 has a diameter greater than the radial thickness of the tubular portion 20 so as to project radially inwardly into engagement with an annular groove 30 formed in the ocular mount 12 and radially outwardly into engagement with a helical groove 31 formed in the collar 26.

The collar 26, tubular portion 20 and ocular mount 12 are thereby keyed together by the cooperating ball bearing 28, groove 30 and groove 31 in a manner which allows the ocular mount to rotate freely relative to the tubular portion 20 but which prevents relative axial movement for any fixed orientation of the collar 26. The collar 26 is fixed axially with respect to the tubular portion 20 so that when the collar 26 is rotated the ball bearing 28, which is constrained to lie at a fixed azimuthal position relative to the optical axis by virtue of the slot 29, is compelled to move axially to an extent defined by the pitch of the helical groove 31 and this axial displacement is accompanied by movement axially of the ocular mount 12 to which the ball bearing is keyed via the annular groove 30.

Alternative embodiments of the present invention are envisaged in which the image relaying means may comprise elements other than axially spaced lenses such as for example a coherent fibre optic bundle. In such an arrangement the rotation axis of the tube need not necessarily be coincident with the optical axis of the ocular lens.

In an alternative arrangement the reflector may be rotated relative to the tube by a suitable mechanism provided that an appropriate viewing port enables lateral viewing to be achieved throughout orbital scan.

I claim:

1. Apparatus for use as a borescope, comprising:

a tube having a distal end which is insertable in use into an inaccessible location and a proximal end connected to a housing, a viewing port adjacent the distal end and an associated reflector through which an object at the inaccessible location may be laterally viewed in use, an image relaying means operable to relay an image of the object to a means for viewing provided in the housing, a scanning means operable to rotate the reflector relative to the housing about a rotation axis extending longitudinally of the tube, focusing means operable to adjust the position of the viewing means relative to the housing in the direction along an optical axis defined by the viewing means, and an image inverter operable to correct image inversion created by the reflector, wherein the inverter is rotatably mounted in the housing for rotation about the optical axis, the scanning means is further operable to provide the rotation of the inverter synchronously with the rotation of the reflector, and wherein the viewing means comprises an ocular lens received in an ocular mount with respect to which the inverter is fixedly connected at a location proximal to the ocular lens such that said scanning means rotates said ocular mount with inverter together with said reflector, and said ocular mount and inverter fixed therein being supported by said housing so as to be axially moveable with respect to said reflector.

2. Apparatus as claimed in claim 1 wherein the scanning means is operable to rotate the ocular mount about the optical axis to provide rotation of the inverter.

3. Apparatus as claimed in claim 2 wherein the focusing means comprises a focus actuator operable to provide adjustment along the optical axis of the position of the ocular mount relative to the housing.

4. Apparatus as claimed in claim 3 wherein the ocular mount is slidably received in a tubular portion of the housing and the focus actuator comprises a collar rotatably mounted on the tubular portion, the apparatus further comprising a coupling mechanism operable to axially displace the ocular mount in response to rotation of the collar and allowing the ocular mount to rotate freely relative to the collar in response to rotation of the ocular mount by the scanning means.

5. Apparatus as claimed in claim 4 wherein the coupling mechanism comprises a ball bearing located in an axially extending slot defined by the tubular portion of the housing, the ball bearing projecting radially inwardly and outwardly of the tubular portion into respective engagement with an annular groove formed in a cylindrical surface of the ocular mount and a helical groove formed in the collar.

6. Apparatus as claimed in claim 1 wherein the scanning means is operable to rotate the tube relative to the housing such that the rotation axis of the tube is colinear with the optical axis of the viewing means, the tube being provided with a connecting member operable to impart rotational movement of the tube to rotational movement of the ocular mount, one of the connecting member and the ocular mount being provided with an axially extending slot cooperable with a radially projecting pin mounted on the other.

7. Apparatus as claimed in claim 1 wherein the image relaying means comprises an optical relay having a plurality of lenses spaced axially within the tube.

8. Apparatus as claimed in claim 1 wherein the inverter comprises a dove prism.

9. Apparatus as claimed in claim 8 wherein the effective aperture of the dove prism is at least as large as the effective aperture of the ocular lens.

10. Apparatus for use as a borescope, comprising:

a housing having a first end, a second end and a tubular portion therebetween;

a tube having a distal end which is insertable in use into an inaccessible location and a proximal end connected to the housing, said tube having a viewing port adjacent the distal end, a reflector supported at the distal end of said tube;

image relaying means for relaying an image received through the viewing port and to the reflector along said tube;

a tubular connecting member which is rotatably supported in said tubular portion and has a distal end fixed with the proximal end of said tube;

an ocular mount which has a distal end fixed for rotation with said tubular connecting member, and said ocular mount and tubular connecting member being in an axially movable relationship with each other;

an ocular lens positioned within said ocular mount;

an inverter positioned within said ocular mount at a location proximal to the ocular lens;

an annular collar extending about and in sliding engagement with a proximal portion of said tubular portion;

a scanning mechanism which includes a bush that is axially fixed with respect to the first end of said housing, said bush being engaged with said tube such that rotation of said scanning mechanism results in rotation of said tube;

an eyepiece assembly supported at the second end of said housing; and a coupling mechanism operable to axially displace the ocular mount in response ho rotation of the collar, and which coupling mechanism allows the ocular mount to rotate freely relative to the collar in response to rotation of the ocular mount which occurs upon rotation of the scanning mechanism and engaged tube and the tubular connecting member rotatably fixed to said ocular mount.

11. An apparatus as recited in claim 10 wherein said coupling mechanism includes a ball bearing and the tubular portion of said housing includes an axially extending slot and said ocular mount and collar each including a reception slot with one of said slots being in the form of a helical groove.

12. An apparatus as recited in claim 10 wherein said tubular connecting member and said ocular mount are engaged so as to rotate at a common rate with said tube.

13. An apparatus as recited in claim 10 wherein said inverter has on the effective aperture that is larger than the effective aperture of the ocular lens.

14. An apparatus as recited in claim 10 wherein said eyepiece is fixed to said housing and remains stationary while said collar is rotated with respect to said housing.

15. An apparatus as recited in claim 10 wherein one of said ocular mount and tubular connecting member includes a longitudinal slot while an opposite one of said ocular mount and tubular connecting member includes a pin which extends into said slot, whereby one of said ocular mount and tubular connecting member is axially movable with respect to the other and an assembly of said ocular mount and tubular portion are fixed for rotating as a common assembly.

* * * * *